US00PP10949P

United States Patent [19]

Pouw

[11] Patent Number: Plant 10,949

[45] Date of Patent: Jun. 8, 1999

[54] HYBRID TEA ROSE PLANT NAMED 'PANRAV'

[75] Inventor: A. A. Pouw, De Kwakel, Netherlands

[73] Assignee: Panorama Roses N.V., Curacao, Netherlands

[21] Appl. No.: 08/982,492

[22] Filed: Dec. 2, 1997

[51] Int. Cl.[6] ..... A01H 5/00

[52] U.S. Cl. ..... Plt./139

[58] Field of Search ..... Plt./19, 20, 130, Plt./138, 139

*Primary Examiner*—Howard J. Locker

*Attorney, Agent, or Firm*—Christie, Parker & Hale, LLP

[57] ABSTRACT

A new variety of hybrid tea rose plant producing red flowers of good form and suitable for growing under glass.

1 Drawing Sheet

BACKGROUND OF THE INVENTION

The present invention relates to a new and distinct variety of rose plant of the hybrid tea rose class which was created by crossing undistributed, unnamed and unpatented seedlings as seed and pollen parents in Quito, Ecuador. The varietal denomination of the new variety is 'Panrav'. The new variety was isolated and asexually reproduced by budding in Quito, Ecuador.

SUMMARY OF THE INVENTION

Among the novel characteristics possessed by this new variety which distinguish it from its parents and all other varieties of which I am aware are its attractive red flowers of good form with long stems borne on a floriferous plant and suitable for production of cut flowers under glass.

Asexual reproduction by budding of the new variety as performed in Quito, Ecuador, shows that the foregoing and other distinguishing characteristics come true to form and are established and transmitted through succeeding propagations. The new variety has been reproduced through propagation by cuttings, grafting, budding and micropropagation.

BRIEF DESCRIPTION OF ILLUSTRATION

The accompanying illustration shows a typical specimen of the vegetative growth and flowers of the new variety as a cut flower, depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart. Phenotypic expression may vary depending upon growing conditions under different climate, soil, and cultivation conditions.

Parentage: Seed and pollen parents are unnamed seedlings. Class: Hybrid Tea.

The following further horticultural description is based on observations made of specimens grown under glass in Quito, Ecuador.

FLOWER

Blooming habit: Nearly continuous, about 190 stems/$m^2$/year.

A. Bud:

(1) *Size.*—Medium, about 4 cm long by about 4 cm wide after sepals fall.

(2) *Form.*—Ovate (shape of longitudinal section just before separation of sepals); urn-shaped after sepals part and petals begin to separate.

(3) *Color.*—Near 54A to 52A after sepals separate.

(4) *Sepals.*—Longer than bud, some foliaceous; near 136C to 137C on top surface, some with dark green or purplish ends, near 137B undersurface.

(5) *Peduncle.*—Long, about 9.5 cm; Strength-erect, strong. Color-medium green, near 139A to 139B.

B. Flower: Medium; viewed from above — star-shaped; viewed from side — (a) upper part of fully opened flower, flattened, convex; (b) lower part of fully opened flower, flat.

(1) *Size.*—Average size when fully expanded — about 10 cm at near full open.

(2) *Borne.*—Singly, one to a stem.

(3) *Form.*—Pointed center, spiral imbricated, outer petals reflex to points; some inner petals reflex to points and some roll under.

(4) *Petalage.*—Fully double, about 23 petals.

(5) *Color.*—After sepals part and petals unfurl color of petal top surface appears near 52A to 52B, (⅓ to full open); Petal undersurface tends to near 52A but displays light red to pink washing toward point of petal attachment. Color at point of petal attachment is near 12A. Overall tonality from a distance is attractive red, near 52A and 52B.

(6) *Peduncle.*—Generally smooth.

(7) *Fragrance.*—Absent or weak.

(8) *Length of stems.*—About 50 to 100 cm.

Petals:

(1) *Texture.*—Crisp.

(2) *Appearance.*—Inside velvety and outside satiny to matte.

(3) *Form and size.*—Broad, medium, medium undulation of margin.

(4) *Arrangement.*—Regularly arranged, imbricated.

(5) *Petaloids.*—About 1 to 3, most with white stripe.

(6) *Lasting quality.*—Long-lasting quality on plant, about 14 days, and after cutting, about 12 days.

REPRODUCTIVE ORGANS

A. Stamens, filaments and anthers:
*Arrangement and color.*—Regularly arranged around styles; color of filaments — pink.
B. Pollen:
*Color.*—Near 13D.
C. Styles: Long, stigma above mouth of receptacle, pale yellow.
D. Stigmas: Yellow, positioned below anthers.
E. Hip: Pear-shaped, medium seed vessel at petal fall.

PLANT

A. Form: Narrow, bushy, average disease resistance, height about 178 cm, spread about 50 cm.
B. Growth: Vigorous.
C. Foliage: Compound 3, 5 and 7 leaflets.
(1) *Size.*—3-leaflet leaf, terminal leaflet about 8 cm long; 5-leaflet leaf, terminal leaflet about 7 cm long; 7 leaflet leaf, terminal leaflet about 6.5 to 7 cm long.
(2) *Quantity.*—Abundant.
(3) *Color.*—Juvenile foliage — upper side near 187A to 187B; under side near 187C; medium anthocyanin coloration, (shoot about 20 cm long); mature leaf color — upper side near 139A, under side near 137C.
(4) *Shape.*—Broad oval.
(5) *Texture.*—Upper side is medium glossy; underside is matte.
(6) *Edge.*—Serrate.
(7) *Serration.*—Ordinary, acuminate apices.
(8) *Leaf stem.*—Color — near 139C.
(9) *Stipules.*—Short to medium, simple, medium green with light mid line.
(10) *Leaflets.*—Cross section — flat: absent or weak undulation of margin; terminal leaflet — medium length and medium width; obtuse base.
D. Wood:
(1) *New wood.*—Color — young shoots have weak anthocyanin; coloration — bronze red purple to reddish brown.
(2) *Old wood.*—Color — near 147A to 147B.
E. Prickles (thorns):
(1) *Prickles.*—Present; quantity (main stalk) — ordinary; shape of lower side — concave; Length — short prickles few, long prickles few to medium; Color — near 173A; Position — irregular.

What is claimed is:

1. A new and distinct rose plant of the variety substantially as shown and described.

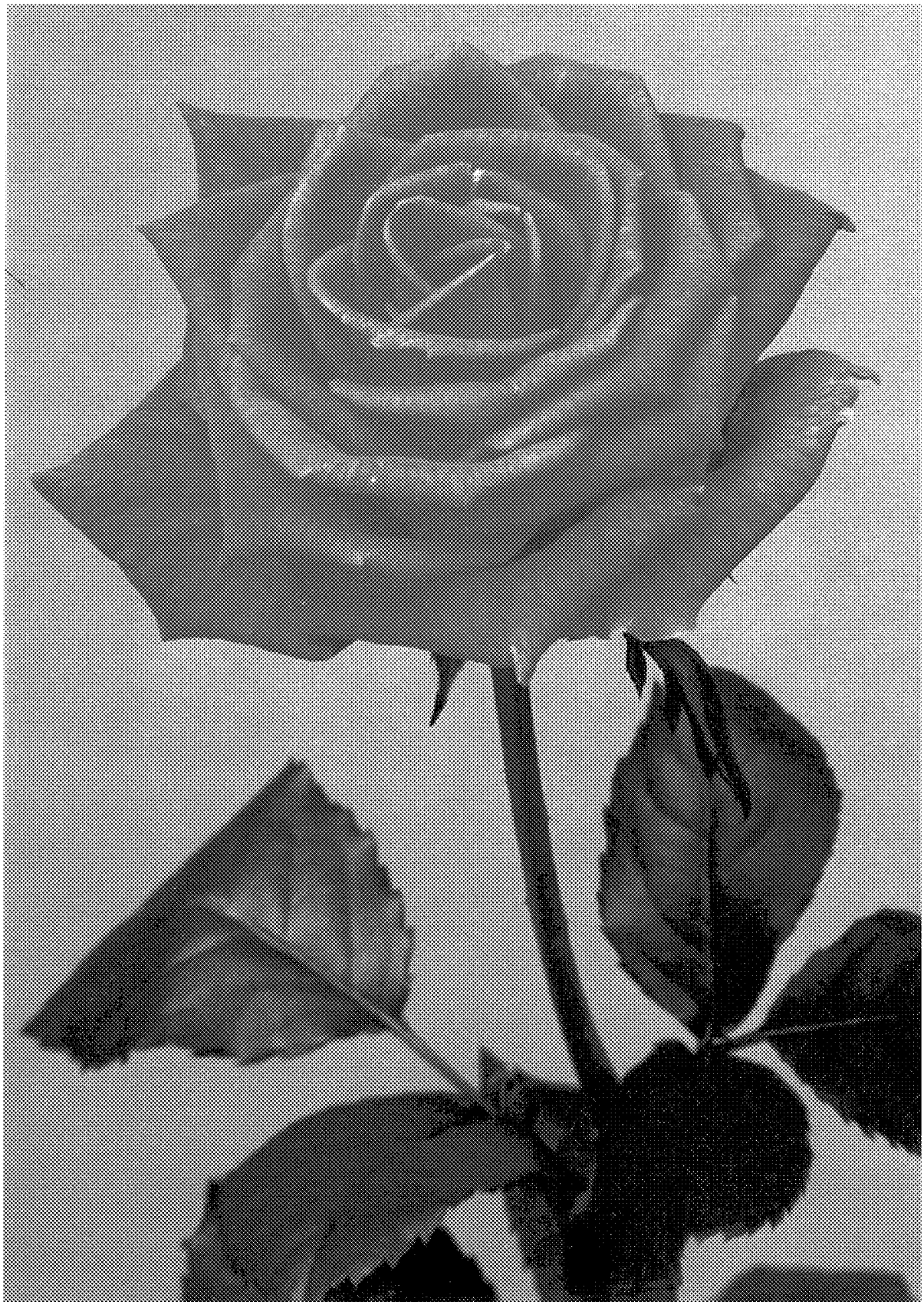

* * * * *